United States Patent [19]
Harris

[11] Patent Number: 5,498,598
[45] Date of Patent: Mar. 12, 1996

[54] COMPOSITION FOR NASAL ADMINISTRATION OF DESMOPRESSIN

[75] Inventor: Alan Harris, Malmo, Sweden

[73] Assignee: Ferring AB, Malmo, Sweden

[21] Appl. No.: 430,131

[22] Filed: Apr. 25, 1995

Related U.S. Application Data

[63] Continuation of Ser. No. 84,894, Jun. 29, 1993, abandoned.

[51] Int. Cl.$^6$ ............................ A61K 38/16; A61K 38/21
[52] U.S. Cl. ............................................................ 514/11
[58] Field of Search .................................................. 514/11

[56] References Cited

U.S. PATENT DOCUMENTS

| | | |
|---|---|---|
| 3,794,633 | 2/1974 | Kamber et al. . |
| 3,929,758 | 12/1975 | Hughes et al. . |
| 4,033,940 | 7/1977 | Hughes et al. . |
| 4,093,610 | 6/1978 | Abraham et al. . |
| 4,216,141 | 8/1980 | Rivier et al. . |
| 4,271,068 | 6/1981 | Kamber et al. . |
| 4,351,764 | 9/1982 | Birr . |
| 4,487,765 | 12/1984 | de Wied . |
| 4,985,242 | 1/1991 | Sekine et al. . |
| 5,066,716 | 11/1991 | Robey et al. . |
| 5,124,315 | 6/1992 | Ceschel et al. . |

FOREIGN PATENT DOCUMENTS

| | | | |
|---|---|---|---|
| 0381345 | 8/1990 | European Pat. Off. . | |
| PCTWO88/05661 | 8/1988 | WIPO . | |

OTHER PUBLICATIONS

Andersson et al., *DDAVP: Pharmacology and Clinical Use*, Drugs of Today, 1988, 24(7):509–528.
Vavra, Effect Of A Synthetic Analogue Of Vasopressin In Animals And In Patient With Diabetes Insipidue, Lancet, pp. 948–952 (1968).
Harris et al., J. of Pharm. Sci., vol. 77, No. 4, pp. 337–339 (1988).
Anik et al., J. of Pharm. Sci., vol. 73, No. 5, pp. 684–685 (1984).

*Primary Examiner*—Johann Richter
*Assistant Examiner*—John Peabody
*Attorney, Agent, or Firm*—Hopgood, Calimafde Kalil & Judlowe

[57] ABSTRACT

An aqueous composition for spray nasal administration of a synthetic analog of vasopressin (desmopressin; actate containing between 2.5 and 7.5 μg per 100 μl. The composition may additionally contain an osmotic-pressure controlling agent, such as sodium chloride, a preservative, such as chlorobutanol or benzalkonium chloride, and a buffer stabilizing the pH between about 4 and 6. Buffers containing citrate and/or phosphate are preferred. Also disclosed is a sealed container filled with the composition, an assembly comprising the container and a spray pump, and the use of the composition, the container, and the assembly in the management of urinary disorders.

10 Claims, 1 Drawing Sheet

COMPOSITION FOR NASAL ADMINISTRATION OF DESMOPRESSIN

The constant case is a File-Wrapper continuation Ser. No. 08/084,894, filed Jun. 29, 1993, now abandoned.

FIELD OF THE INVENTION

The present invention is a composition for spray delivery to the nasal mucosa of 1-deamino-8-D-arginine-vasopressin (desmopressin).

BACKGROUND

Desmopressin, 1-(3-mercaptopropionic acid)-8-D-arginine-vasopressin (hereinafter also abbreviated as "DDAVP") is an analog of the neurohypophyseal peptide vasopressin. DDAVP is indicated in the management of a variety of medical conditions such as irregular urination or diurea, particularly those associated with diabetes insipidus and nocturnal enuresis.

DDAVP is currently available as an aqueous nasal spray composition which is administered by means of a metered spray pump. For instance, MINIRIN® nasal spray, Ferring AB, Sweden, contains 10 µg of desmopressin acetate per 100 µl, 0.5% of chlorobutanol (w/v) as preservative, and sodium chloride. Intranasal administration of about 200 µl MINIRIN® spray, containing about 20 µg of desmopressin, provides an antidiuretic effect lasting in most adult patients for about 8 to 12 hours. In a minority of cases a dose of up to 40 µg (400 µl) is required for similar effects.

For most nasally administered agents, the capacity of the human nasal cavity surface for holding aqueous solutions is limited. In most adults, this capacity is about 400 µl. For efficient systemic absorption of nasally administered therapeutics, the vehicle carrying the drug must remain in contact with the mucus-lined epithelium for a sufficient period of time.

400 µl volume is close to the maximum useful volume for known nasal spray compositions containing desmopressin. Nasal spray compositions having low concentrations of DDAVP might allow coverage of a wider range of patients, such as including very young or elderly patients. However, even such dilute concentrations must be delivered in minute doses because of the potency of DDAVP. On the other hand, about 100 µl (containing a dose of 10 µg) of known solutions containing DDAVP is the lowest dose volume that can be conveniently reproduced by single actuations of the metered spray pump, and remain therapeutically effective.

Harris et al., *J. Pharm. Sci.* 77 (1988) 337–339, conducting experiments based on healthy human volunteers, state that a given amount of desmopressin in larger volume, when given in a single dose, is absorbed substantially less effectively than the same amount in a smaller volume (see FIG. 1, Harris, ibid.). These findings are in full agreement with those of Anik et al., *J. Pharm. Sci.* 73 (1984) 684–685, who conducted similar tests on rhesus monkeys with nasally administered solutions containing the decapeptide nafarelin acetate. Both reports favor higher concentrations and discourage use of more dilute solutions.

The known results obtained with desmopressin are based on analysis of plasma levels of desmopressin and factor VIII:C. The release into plasma of factor VIII:C is known to be stimulated by high doses of desmopressin. The dosage administered intranasally in such experiments was approximately 300 µg, about ten times the average dose given to patients with urinary disorders.

Thus, there exists a problem in the art for achieving a balance between therapeutic needs and dosage related problems of DDAVP nasal compositions. There is a need in the art for precisely metered, easily administered, and consistently reproducible nasal delivery compositions containing DDAVP.

OBJECTS OF THE INVENTION

An object of the present invention is to provide a nasal spray composition containing desmopressin which allows effective delivery to a wider range of patients, including very young and elderly patients.

Another object is to provide an aqueous composition for nasal administration of between 2.5 and 7.5 µg of desmopressin per 100 µl, which allows consistent delivery of optimum therapeutic doses of the DDAVP.

Further objects include the provision of a sealed container for delivery of DDAVP nasal compositions, an assembly comprising the sealed container and a spray pump, and the use of the composition, the container, and the assembly in the management of urinary disorders.

SUMMARY OF THE INVENTION

It has now been surprisingly found that the known relationship between the concentration of desmopressin in the aqueous carrier for nasal spray administration, said concentration being a desmopressin concentration of at least 10 µg per 100 µl, and desmopressin uptake by the nasal mucosa, which relationship dissuades from using more dilute solutions, does not hold for substantially smaller desmopressin concentrations, such as concentrations ranging from 2.5 µg to 7.5 µg per 100 µl.

In accordance with the invention, there is disclosed an aqueous nasal spray composition containing between 2.5 and 7.5 µg of desmopressin per 100 µl, the preferred concentration being about 5 µg desmopressin per 100 µl aqueous composition. It has been unexpectedly found that these optimum ranges provide ideal nasal delivery conditions for optimal therapeutic effects for desmopressin.

A preferred embodiment of the composition according to the present invention comprises an osmotic pressure-controlling agent, such as sodium chloride, and a preservative, such as chlorobutanol or a quaternary amine preservative such as benzalkonium chloride.

According to another embodiment, the composition additionally comprises a buffer, preferably a buffer comprising citrate and/or phosphate. The buffer used in the present compositions should maintain the pH from about 4 to about 6, preferably a pH of about 5.

It is especially preferred for the composition to comprise both benzalkonium chloride and the above-defined buffer, which makes the DDAVP nasal compositions of the present invention room-temperature stable, with shelf lives exceeding one year.

Additionally the composition according to the invention may contain absorption enhancers such as bile salts, monolauryl ethers of macrogols, phospholipids and fusidate derivatives.

It is preferred for the composition according to the invention to be administrable in a metered dose or multiples thereof, said metered dose comprising from 2.5 µg to 7.5 µg of desmopressin dissolved in from 50 µl to 150 µl of an aqueous carrier to provide a desmopressin concentration in said carrier ranging from 2.5 μg to 7.5 μg per 100 μl, for effecting a plasma profile essentially corresponding to that obtainable by single or multiple dose nasal administration of the same total amount of desmopressin dissolved in said carrier in substantially higher concentration.

It is also preferred for the composition according to the invention to be administrable in a metered dose or multiples thereof, said metered dose comprising from 2.5 μg to 7.5 μg of desmopressin dissolved in from 50 μl to 150 μl of an aqueous carrier, for effecting a plasma profile essentially equivalent, on a desmopressin unit dose weight basis, to a desmopressin plasma profile obtainable by nasal administration of a metered dose of desmopressin comprising substantially higher amounts of desmopressin in a corresponding smaller volume of aqueous carrier ranging from 50 μl to 150 μl.

Also disclosed is a sealed container filled with an aqueous desmopressin spray composition according to the invention and its use in connection with a spray pump. The container and the pump may be integrated as a unit and can also be made disposable. It is preferred for the pump to be a metered precompression spray pump. The pump is preferably designed for delivering a dose ranging from 2.5 to 7.5 μg desmopressin per actuation, with the optimum amount at about 5 μg.

The composition according to the invention is used for effective therapeutic management of various urinary disorders, such as diabetes insipidus, incontinence, and enuresis, particularly nocturnal enuresis.

DETAILED DESCRIPTION

Figure 1:
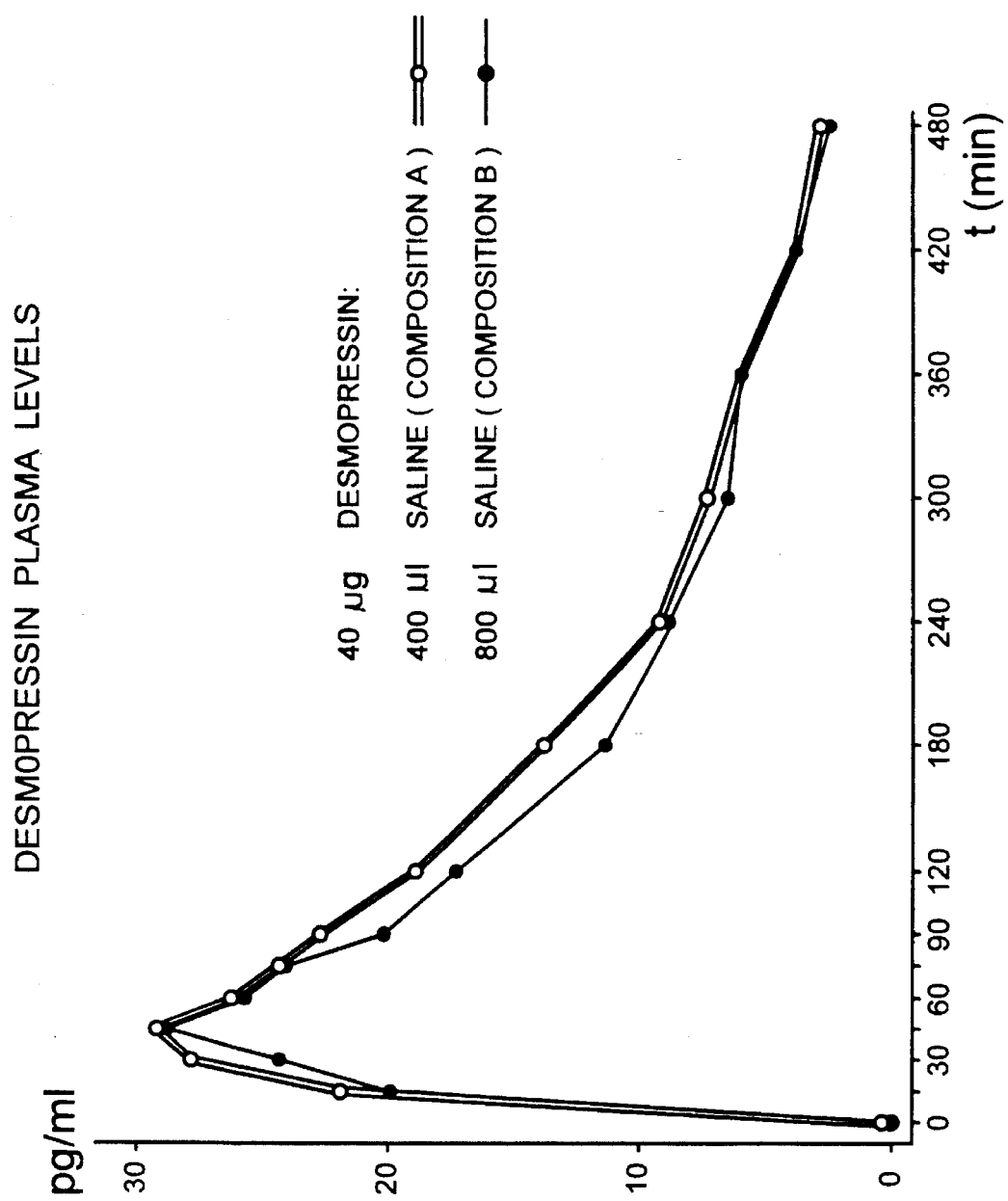
FIG. 1 graphically depicts therapeutical bioequivalence of known DDAVP nasal solutions and the DDAVP aqueous nasal compositions of the present invention.

The invention will now be explained in detail by reference to the following experimental examples.

EXAMPLE 1

PREPARATION OF TEST SOLUTIONS

Two desmopressin acetate nasal spray compositions (A and B) were prepared under aseptic conditions by dissolving the following components in 1 l of Millipore®-filtered water:

| composition | A | B |
| --- | --- | --- |
| desmopressin acetate | 100 mg | 50 mg |
| chlorobutanol* | 5 g | 5 g |
| sodium chloride | 9 g | 9 g |

*1,1,1-trichloro-2-methylpropan-2-ol pH was adjusted to 3.5–5.0 by addition of 2 N HCl. A denotes a currently known composition which was prepared for comparison, while B denotes the composition made according to the present invention.

EXAMPLE 2

COMPARATIVE TESTING 24 healthy male volunteers were given 40 μg of desmopressin in the form of composition A from Example 1 (administration of a 4×100 μl=400 μl dose). After an interval of at least one week, the same test subjects were given desmopressin in the form of composition B (administration of a 8×100 μl= 800 μl dose). Commercially available, metered-dose spray pumps manufactured by Erich Pfeiffer AG, Rudolfzell, Germany, set to the appropriate dosage volumes were used.

Blood was collected by venipuncture before administration (control) and at times 5, 15, 30, 45, 60, and 90 minutes, and 2, 4, 6, and 8 hours after administration. Plasma desmopressin was assayed by RIA as described by Harris, et al., *J. Pharm. Sci.* 77 (1988) 337–338 (for statistical treatment of data, see Harris ibid., p. 338).

The results are graphically depicted in FIG. 1, which shows plasma levels of desmopressin as a function of time. It is evident from FIG. 1 that composition (A) and the composition according to the present invention (B) are bioequivalent and therefore therapeutically equivalent. It can also be seen that composition (B) has a substantially broader useful administration range.

EXAMPLE 3

LONG SHELF-LIFE COMPOSITION

A nasal spray composition according to the present invention having a shelf life of more than one year at room temperature was prepared by dissolving in 1000 ml of Millipore®-filtered water: 50 mg of desmopressin acetate, 1.0 g of benzalkonium chloride, 6.3 g of sodium chloride, 1.56 g of citric acid, and 2.43 g of disodium hydrogen phosphate.

While the various embodiments of the present invention have been described herein, it is possible that one skilled in the art could modify the various reagents and reaction conditions and obtain similar results. Such modifications are contemplated as being within the scope of the present disclosure.

What is claimed is:

1. An aqueous composition for intra-nasal administration of desmopressin, comprising between about 2.5 and about 7.5 μg desmopressin acetate per 100 μl of said aqueous composition.

2. The composition according to claim 1, wherein said composition contains about 5 μg desmopressin acetate per 100 μl.

3. The composition according to claim 1, further comprising a sodium chloride osmotic pressure-controlling agent.

4. The composition according to claim 1, further comprising a preservative selected from the group consisting of chlorobutanol and benzalkonium chloride.

5. The composition according to claim 1, further comprising a buffer selected from the group of buffers consisting of citrate, phosphate, and a mixture of citrate and phosphate.

6. The composition according to claim 5, wherein said buffer maintains a pH from about 4 to about 6.

7. The composition according to claim 6, wherein said buffer maintains pH at about 5.

8. The composition according to claim 1, further comprising at least one absorption enhancing agent selected from the group consisting of bile salts, monolauryl ethers of macrogols, phospholipids and fusidate derivatives.

9. The composition according to claim 1, administrable in a metered dose or multiples thereof, said metered dose comprising from 2.5 μg to 7.5 μg of desmopressin acetate dissolved in from 50 μl to 150 μl of an aqueous carrier to provide a desmopressin concentration in said carrier ranging from 2.5 µg to 7.5 µg per 100 µl, for effecting a plasma profile essentially corresponding to that obtainable by nasal administration of the same total amount of desmopressin dissolved in said carrier in substantially higher concentration.

10. The composition according to claim 1, administrable in a metered dose comprising from 2.5 µg to 7.5 µg of desmopressin acetate dissolved in from 50 µl to 150 µl of an aqueous carrier, for effecting a plasma profile essentially equivalent, on a desmopressin unit dose weight basis, to a desmopressin plasma profile obtainable by nasal administration of a metered dose of desmopressin comprising substantially higher amounts of desmopressin in a corresponding smaller volume of aqueous carrier ranging from 50 µl to 150 µl.

* * * * *